(12) United States Patent
Sakai et al.

(10) Patent No.: US 9,601,224 B2
(45) Date of Patent: Mar. 21, 2017

(54) ELECTRON BEAM IRRADIATION APPARATUS

(71) Applicant: HITACHI ZOSEN CORPORATION, Osaka (JP)

(72) Inventors: Ichiro Sakai, Osaka (JP); Takayasu Yokobayashi, Osaka (JP)

(73) Assignee: Hitachi Zosen Corporation, Osaka (JP)

( * ) Notice: Subject to any disclaimer, the term of this patent is extended or adjusted under 35 U.S.C. 154(b) by 0 days.

(21) Appl. No.: 14/785,091

(22) PCT Filed: Apr. 9, 2014

(86) PCT No.: PCT/JP2014/060236
§ 371 (c)(1),
(2) Date: Oct. 16, 2015

(87) PCT Pub. No.: WO2014/175065
PCT Pub. Date: Oct. 30, 2014

(65) Prior Publication Data
US 2016/0064111 A1 Mar. 3, 2016

(30) Foreign Application Priority Data

Apr. 26, 2013 (JP) ................. 2013-093145

(51) Int. Cl.
*G21K 5/00* (2006.01)
*G21K 5/04* (2006.01)
(Continued)

(52) U.S. Cl.
CPC .............. *G21K 5/04* (2013.01); *A61L 2/087* (2013.01); *B65B 55/08* (2013.01); *G21K 5/00* (2013.01); *A61L 2202/23* (2013.01)

(58) Field of Classification Search
USPC .......................................... 250/493.1, 496.1
See application file for complete search history.

(56) References Cited

U.S. PATENT DOCUMENTS 5,949,080 A 9/1999 Ueda et al.
2008/0073549 A1 3/2008 Avnery

FOREIGN PATENT DOCUMENTS

AU 684652 2/1996
JP 6-289200 10/1994
(Continued)

OTHER PUBLICATIONS

English language machine translation of JP 7-18299.
(Continued)

*Primary Examiner* — Nicole Ippolito
*Assistant Examiner* — Hanway Chang
(74) *Attorney, Agent, or Firm* — Fildes & Outland, P.C.

(57) ABSTRACT

An electron beam irradiation apparatus that emits an electron beam into a container, the electron beam irradiation apparatus including: a vacuum housing constituting a vacuum chamber; an electron generator provided in the vacuum housing; a cylindrical nozzle member that is extended from the vacuum housing so as to be inserted into the container and has exit windows on the distal end of the nozzle member, the exit windows being provided for emission of an electron beam generated by the electron generator into the container; and a magnetic shield member for the vacuum chamber and a magnetic shield member for the nozzle member, the magnetic shield members being respectively provided for the vacuum housing and the nozzle member so as to block variable magnetism generated around an electron beam trajectory extended from the electron generator to the exit windows.

11 Claims, 8 Drawing Sheets

(51) Int. Cl.
*B65B 55/08* (2006.01)
*A61L 2/08* (2006.01)

(56) References Cited

FOREIGN PATENT DOCUMENTS

| | | |
|---|---|---|
| JP | 7-18299 | 3/1995 |
| JP | 9-507913 | 8/1997 |
| JP | 2009-526971 | 7/2009 |

OTHER PUBLICATIONS

English language machine translation of JP 6-289200.
Extended European Search Report in European Patent Application No. 14787464.8 dated Nov. 30, 2016.

ELECTRON BEAM IRRADIATION APPARATUS

TECHNICAL FIELD

The present invention relates to an electron beam irradiation apparatus that emits an electron beam into a container.

BACKGROUND ART

An electron beam irradiation apparatus conventionally used for sterilization in a container with a narrow neck includes: a vacuum chamber; an electron generator provided in the vacuum chamber; and a cylindrical nozzle member that is extended from the vacuum chamber so as to be inserted into the container from the neck and has exit windows on the distal end of the nozzle member, the exit windows being provided for emission of electron beams generated by the electron generator (For example, Patent Literature 1). As shown in FIG. 3, a nozzle member 14 is inserted into a container 18 from the neck of the container, and then electron beams are emitted from the distal end of the nozzle member 14 to clean the inside of the container 18.

Although electron beams are widely emitted from the exit windows provided on the distal end of the nozzle member 14, a reduction in electron dose may limit a sterilisation range and thus the exit windows need to be brought close to the bottom of the container 18. This requires the length of the nozzle member 14 to be substantially equal to the height of the container 18. If the container 18 is tall, the nozzle member 14 may be 30 cm to 40 cm in length. Moreover, the nozzle member 14 needs to have an outside diameter (e.g., about 10 mm) so as to be loosely fit into the mouth of the container 18. Thus, the nozzle member 14 requires a slender shape. Furthermore, in order to stably emit electron beams into the container 18, electron beams need to pass through in an elongated shape in the nozzle member 14, that is, an electron beam trajectory needs to be elongated in the nozzle member 14.

CITATION LIST

Patent Literature

Patent Literature 1: National Publication of International Patent Application No. 2003-526971

SUMMARY OF INVENTION

Technical Problem

In the electron beam irradiation apparatus including the nozzle member 14 as described in Patent Literature 1, however, the elongated electron beam trajectory in the nozzle member 14 may be affected by the magnetism of the earth or peripheral devices including a motor. More specifically, the electron beam trajectory may be curved by the influence of magnetism so as to emit electron beams only partially from the exit windows or allow electron beams to collide with the inner surface of the nozzle member 14 before reaching the exit windows. This cannot stably emit electron beams with desired intensity from the exit windows, disadvantageously leading to unstable sterilisation in the container. The intensity of the earth's magnetism considerably fluctuates depending on solar activities such as a magnetic storm or positions on the surface of the earth, or is considerably affected by magnetic fields parallel to the surface of the earth from the north pole to the south pole.

An object of the present invention is to provide an electron beam irradiation apparatus that can stably emit electron beams with desired intensity so as to stably sterilize the inside of a container while preventing the magnetism of the earth or peripheral devices from affecting an electron beam trajectory extended from an electron generator to an exit window.

Solution to Problem

The present invention is configured as follows:
(1) An electron beam irradiation apparatus that emits an electron beam into a container, the electron beam irradiation apparatus including: a vacuum chamber; an electron generator provided in the vacuum chamber; a cylindrical nozzle member that is extended from the vacuum chamber so as to be inserted into the container and has exit windows on the distal end of the nozzle member, the exit windows being provided for emission of an electron beam generated by the electron generator into the container; and a magnetic shield member for the vacuum chamber, the shield member being provided for the vacuum chamber so as to block variable magnetism generated around an electron beam trajectory extended from the electron generator to the exit windows.
(2) The electron beam irradiation apparatus according to (1) further includes a magnetic shield member for the nozzle member, the shield member being provided for the nozzle member so as to block variable magnetism generated around the electron beam trajectory extended from the electron generator to the exit windows.
(3) In the electron beam irradiation apparatus according to (2), the magnetic shield member for the vacuum chamber and the magnetic shield member for the nestle member are made of a high permeability material having relative permeability of at least 50000.
(4) In the electron beam irradiation apparatus according to one of (2) and (3), the magnetic shield member for the nozzle member is disposed to surround the electron beam trajectory.
(5) In the electron beam irradiation apparatus according to (4), the magnetic shield member for the nozzle member is disposed in a shape like one of a cylinder, a ring, and a spiral relative to the axis of the nozzle member.
(6) In the electron beam irradiation apparatus according to one of (2) to (5), the magnetic shield member for the nozzle member is disposed inside the nozzle member and is separated from the distal and of a nozzle by a predetermined distance along the axial direction of the nozzle so as to prevent heat generated near the exit windows during electron beam emission and transmitted to the magnetic shield member for the nozzle member from reducing the relative permeability of the magnetic shield member for the nozzle member.
(7) In the electron beam irradiation apparatus according to one of (2) to (6), the magnetic shield member for the nozzle member and a cooling flow path for passage of a medium for cooling the nozzle member are provided on the side of the nozzle member.

Advantageous Effect of Invention

The present invention can provide an electron beam irradiation apparatus that can stably emit electron beams with desired intensity and stably sterilize the inside of a container while preventing the magnetism of the earth or peripheral devices from affecting an electron beam trajectory extended from an electron generator to exit windows.

DESCRIPTION OF EMBODIMENTS

Figure 1:
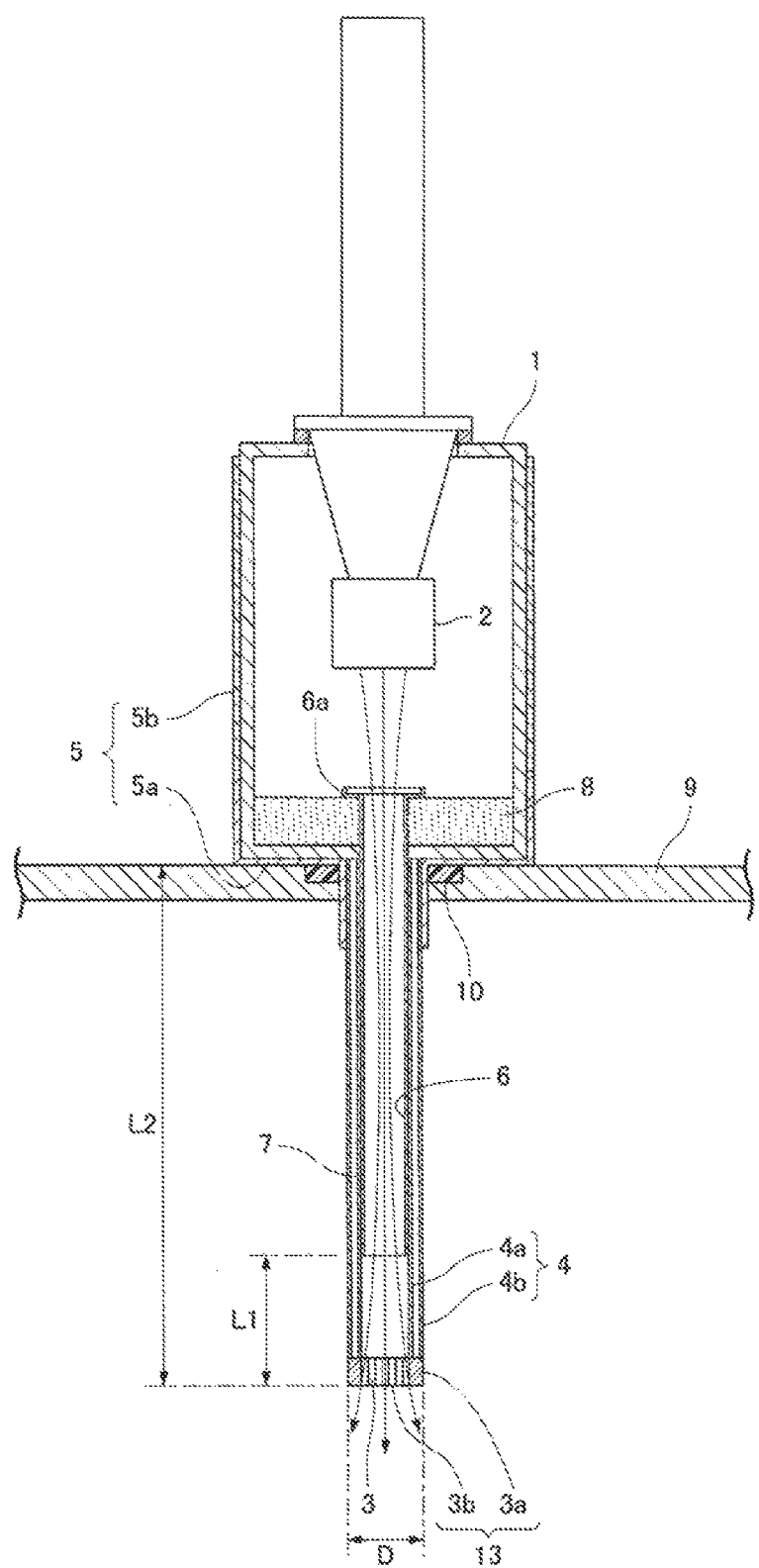
FIG. 1 is a front view showing a part of an electron beam irradiation apparatus in cross section according to a first embodiment of the present invention.

The present invention relates to an electron beam irradiation apparatus that sterilizes the inside of a container (particularly, a container having a narrow neck) by emitting electron beams into the container.

An electron beam irradiation apparatus of the present invention includes: a vacuum chamber; an electron generator provided in the vacuum chamber; a cylindrical nozzle member that is extended from the vacuum chamber so as to be inserted into the container and has exit windows on the distal end of the nozzle member, the exit windows being provided for emission of an electron beam generated by the electron generator into the container; and a magnetic shield member for the vacuum chamber and a magnetic shield member for the nozzle member, the magnetic shield members being respectively provided for the vacuum chamber and the nozzle member so as to block variable magnetism generated around an electron beam trajectory extended from the electron generator to the exit windows. A housing and the nozzle member that constitute the vacuum chamber are composed of, for example, metal, ceramic, or a combination of the metal and the ceramic. The magnetic shield member for the nozzle member is not an essential component.

Using the magnetic shield member for the vacuum chamber and the magnetic shield member for the nozzle member can stably emit an electron beam with desired intensity and stably sterilize the inside of the container while preventing the magnetism of the earth or peripheral devices from affecting the electron team trajectory extended from the electron generator to the exit windows.

The electron beam irradiation apparatus of the present invention includes the long nozzle member that, can emit electron beams into the container. Thus, the electron beam trajectory is extended from the electron generator to the exit windows and electron beams emitted from the electron generator need to pass through the long nozzle member. In the electron beam irradiation apparatus configured thus, the intensity of an electron beam emitted from the exit windows is likely to be greatly changed by the influence of the magnetism of the earth or peripheral devices. Thus, the intensity of an electron beam can be remarkably stabilized using the magnetic shield member for the vacuum chamber and the magnetic shield member for the nozzle member.

The magnetic shield member for the vacuum chamber may be disposed inside or outside the vacuum chamber. The magnetic shield member for the nozzle member may be disposed inside or outside the nozzle member. The magnetic shield member for the nozzle member is preferably disposed in the nozzle member to eliminate the need for changing the outside diameter of the nozzle member to be inserted, into the narrow neck of the container.

The magnetic shield member for the vacuum chamber and the magnetic shield member for the nozzle member are preferably made of a high permeability material having relative permeability of at least 50000. The relative permeability is the value of $\mu/\mu_0$ (relative permeability), the ratio of magnetic permeability $\mu$ to vacuum magnetic permeability $\mu_0$. Such a high permeability material is an alloy containing Ni of 30 to 90 wt % as its principal component. For example, permalloy (Ni—Fe alloy), Supermalloy (Ni—Fe—Mo alloy), Mumetal (Ni—Fe—Cu—Cr alloy), and steel are used.

The magnetic shield member composed of a high permeability material for the vacuum chamber is preferably disposed to surround the electron beam trajectory extended from the electron generator. The magnetic shield member composed of a high permeability material for the nozzle member is preferably disposed in a shape like one of a sheet (cylinder), a ring, a spiral, and a mesh so as to surround the electron beam trajectory. The placement of the shield member can effectively block the magnetism of the earth or peripheral devices.

The magnetic shield member for the nozzle member is preferably separated from the distal end of a nozzle by a predetermined distance along the axial direction of the nozzle so as to prevent heat generated near the exit windows during electron beam emission and transmitted to the magnetic shield member for the nozzle member from reducing the relative permeability of the magnetic shield member for the nozzle member (for example, from reducing the relative permeability to less than 50000).

Electron beams temporarily converge in the nozzle member and then conically spread near the exit windows. Near the exit windows, heat is generated by collision of electron beams to the inner wall of the nozzle member or the inner wall of a support portion constituting the exit window. This may cause a temperature rise to about 300° C. The heat transmitted to the magnetic shield member for the nozzle member may rapidly deteriorate the magnetic shielding effect of the magnetic shield member for the nozzle member. It is known that a high permeability material used for the magnetic shield member for the nozzle member rapidly decreases in permeability when exceeding a certain temperature (e.g., 120° C. 150° C., or 220° C.

This problem can be prevented by separating the magnetic shield member by the predetermined distance.

The magnetic shield member for the nozzle member and a cooling flow path for the passage of a medium for cooling the nozzle member (including the vicinity of the exit windows) are preferably provided on the side of the nozzle member. The magnetic shield member for the nozzle member is more preferably disposed in the cooling flow path. In this case, heat generated near the exit windows during electron beam irradiation does not affect the magnetic shield member and thus the magnetic shield member can be placed not in consideration of the influence of heat. The cooling medium may tae a liquid such as water or gas such as air to be used.

Embodiments of the present invention will be described below with reference to the accompanying drawings. The present invention is not limited to these embodiments.

First Embodiment

Figure 2:
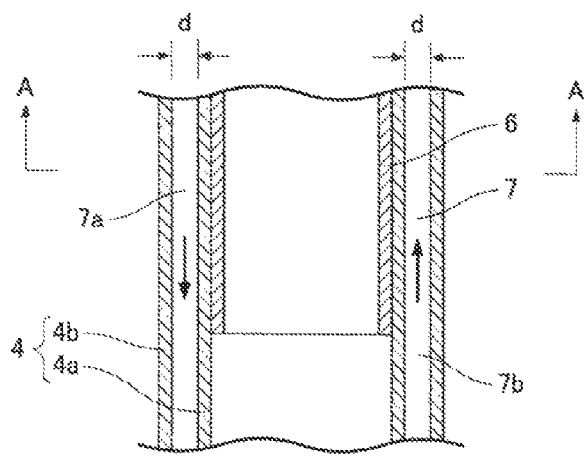
FIG. 2 is a cross-sectional view showing an enlarged part of a nozzle member in the electron beam irradiation apparatus of FIG. 1.

Referring to FIGS. 1 and 2, an electron beam irradiation apparatus according to a first embodiment of the present invention will be described below.

As shown in FIG. 1, the electron beam irradiation apparatus includes a cylindrical vacuum housing 1 that is made of, for example, stainless steel and constitutes a vacuum chamber, an electron generator 2 provided in the vacuum housing 1, a cylindrical nozzle member 4 that is extended from the vacuum housing 1 so as to be inserted into a container from, the neck of the container and has exit windows 3 on the distal end of the nozzle member 4, the exit window 3 being provided for emission of electron beams generated by the electron generator 2, and a magnetic shield member for the vacuum chamber (magnetic shield housing 5) and a magnetic shield member for the nozzle member (magnetic shield cylinder 6), the magnetic shield members being respectively provided for the vacuum housing 1 and the nozzle member 4 so as to block variable magnetism generated around an electron beam trajectory extended, from the electron generator 2 to the exit windows 3.

The nozzle member 4 has a double-pipe structure of a stainless inner nozzle cylinder 4a and a stainless outer nozzle cylinder 4b. The inner nozzle cylinder 4a and the outer nozzle cylinder 4b are disposed substantially on the same axis via a cooling flow path 7 interposed between the nozzle cylinders 4a and 4b. Electron beams pass inside the inner nozzle cylinder 4a. The inner nozzle cylinder 4a is inserted into the hollow part of a support member 8 provided in the vacuum housing 1 so as to be fixed to the vacuum housing 1. The outer nozzle cylinder 4b is fixed such that two ends of the outer nozzle cylinder 4b are attached to the vacuum housing 1 and a support portion 3a, which will be described later.

The inner nozzle cylinder 4a and the outer nozzle cylinder 4b are, for example, 0.5 to 2.0 mm in thickness.

Figure 4:
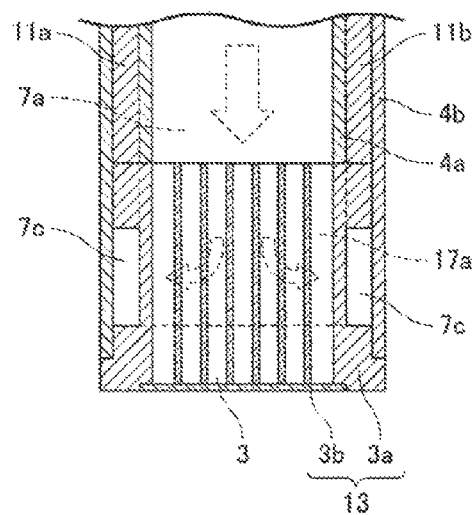
FIG. 4 is a cross-sectional view partially showing a principal part taken along the line B-B of FIG. 3.

As shown in FIGS. 1 and 4, a distal-end member 13 is provided on the distal end of the nozzle member 4. The distal-end member 13 includes the support portion 3a that has the exit windows 3 with a plurality of holes for the flow path of electron beams, and a thin film 3b that covers the surface of the support portion 3a including the exit windows 3. The thin film 3b covering the exit windows 3 can keep a vacuum in the vacuum housing 1. The thin film 3b is, for example, foil of metals such as titanium, tungsten, and gold. The thin film 3b has a thickness of, for example, 4 to 12.5 µm.

Electron beams have a trajectory as indicated by arrows in FIG. 1. Electron beams temporarily converge in the nozzle member 4 and then conically spread near the exit windows 3. Hear the exit windows 3, heat is generated by collision of electron beams to the inner wall of the nozzle member 4 (inner nozzle cylinder 4a) and the inner wall of the support portion 3a. This may cause a temperature rise to about 300° C. In order to reduce the temperature rise near the exit windows 3, the cooling flow path 7 containing a flow of water for cooling in the nozzle member 4 and near the exit windows 3 (support portion 3a) is formed between the inner nozzle cylinder 4a and the outer nozzle cylinder 4b. The cooling flow path 7 is, for example, 0.5 to 1.5 mm in width (a clearance d between the inner nozzle cylinder 4a and the outer nozzle cylinder 4b in a radial direction).

As shown in FIG. 2, the cooling flow path 7 includes a first flow path 7a where cooling water is supplied to the peripheral part of the exit windows 3 (downward in FIG. 2) and a second flow path 2b where cooling water is discharged from the peripheral part of the exit windows 3 (upward in FIG. 2).

Figure 3:
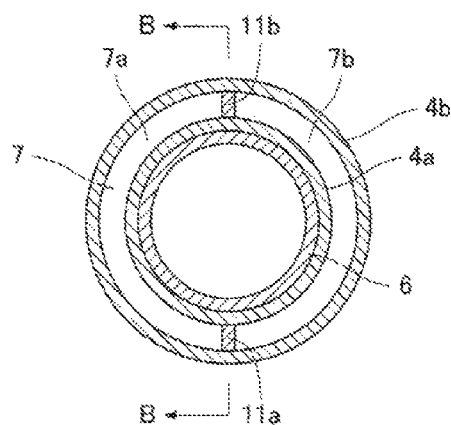
FIG. 3 is a cross-sectional view taken along the line A-A of FIG. 2.

As shown in FIGS. 3 and 4, the first flow path 7a and the second flow path 7b are formed by providing two rod-like partition walls 11a and 11b extended along the axial direction of the nozzle member 4 between the inner nozzle cylinder 4a and the outer nozzle cylinder 4b. The first flow path 7a and the second flow path 7b are opposed to each other with the partition walls 11a and 11b. As shown in FIG. 3, the cooling flow path 7 has a ring-shaped section perpendicular to the axial direction of the nozzle member 4 and the partition walls 11a and 11b are provided so as to divide the ring-shaped cooling flow path 7 substantially into two equal parts.

As shown in FIG. 4, the cooling flow path 7 also has an extended flow path that includes the outer nozzle cylinder 4b and a portion of the support portion 3a extended downward from the inner nozzle cylinder 4a. The extended flow path reaches the peripheral part of the exit windows 3. The support portion 3a further includes a portion extended downward from the rod-like partition walls 11a and 11b, allowing the first flow path 7a and the second flow path 7b to reach the peripheral part of the exit windows 3. Specifically, as shown in FIG. 4, the first flow path 7a has an extended flow path 17a in the peripheral part of the exit windows 3. The second flow path 7b has an extended flow path in a region opposed to the extended flow path 17a.

The first flow path 7a (extended flow path 17a) is connected to the second flow path 7b (extended flow path) via opening portions 7c formed below the partition walls 11a and 11b, respectively. The opening portion 7c is formed using the support portion 3a and the outer nozzle cylinder 4b. Cooling water sequentially passes through the first flow path 7a, the opening portion 7c, and the second flow path 7b.

A supply port (not shown) for cooling water is provided near the upper end of a portion of the outer nozzle cylinder 4b, the portion constituting the first flow path 7a. A discharge port (not shown) for cooling water is provided near the upper end of a portion of the outer nozzle cylinder 4b, the portion constituting the second flow path 7b. This configuration can sequentially supply cooling water to the peripheral part of the exit windows 3, reducing a temperature rise around the nozzle member 4 and the exit windows 3 (support portion 3a). Water discharged from the discharge port may be reused as cooling water.

The magnetic shield member for the vacuum chamber includes the magnetic shield housing 5 having high magnetic permeability and covers the outer surface of the vacuum housing 1. This configuration can suppress the influence of the magnetism of the earth or peripheral devices on an electron beam trajectory extended from the electron generator 2 in the vacuum housing 1 to the nozzle member 4.

The magnetic shield housing 5 includes two components 5a and 5b that are attached onto the vacuum housing 1 from the nestle member and the opposite side from the nozzle member, placing the magnetic shield housing 5 onto the vacuum housing.

The magnetic shield housing 5 has a thickness of, for example, 0.5 to 1.5 mm. The magnetic shield housing 5 is, for example, a Mumetal housing having a thickness of about 0.8 mm and relative permeability of about 90000.

As shown in FIGS. 1 and 2, the magnetic shield member for the nozzle member includes the magnetic shield cylinder 6 having high magnetic permeability and covers the inner surface of the inner nozzle cylinder 4a. This configuration can suppress the influence of the magnetism of the earth or peripheral devices on an electron beam trajectory in the nozzle member 4.

The magnetic shield cylinder 6 is tightly inserted into the inner nozzle cylinder 4a so as to be placed into the nozzle member 4. The magnetic shield cylinder 6 can be placed into the nozzle member 4 only by insertion into the inner nozzle cylinder 4a. This eliminates the need for joining such as welding, advantageously increasing productivity.

The magnetic shield cylinder 6 preferably has a thickness of 0.1 to 0.4 mm, more preferably 0.2 to 0.3 mm.

The magnetic shield cylinder 6 having a thickness of at least 0.1 mm can obtain a sufficient magnetic shielding effect against the electron beam trajectory in the nozzle member 4. Moreover, the magnetic shield cylinder 6 can be sufficiently strong and thus is not deformed or broken when being inserted into the inner nozzle cylinder 4a. If the magnetic shield cylinder 6 is 0.4 mm or less in thickness, a sufficient space for the passage of electron beams can be obtained in the inner nozzle cylinder 4a.

The thickness of the magnetic shield cylinder 6 is not limited to this range and may be optionally changed depending on the output of electron beams, the degree of influence of magnetism, and so on.

The magnetic shield cylinder 6 is, for example, a Mumetal cylinder having a thickness of about 0.25 mm and relative permeability of about 90000.

One end of the magnetic shield cylinder 6 (near the electron generator 2) has a projecting portion 6a that extends outward perpendicularly to the axial direction. The projecting portion 6a can prevent the magnetic shield cylinder 6 from being displaced in the inner nozzle cylinder 4a.

If the magnetic shield cylinder 6 covers the inner surface of the inner nozzle cylinder 4a, heat generated near the exit windows 3 during electron beam irradiation is directly transmitted to the magnetic shield cylinder 6. This may disadvantageously reduce the relative permeability of the magnetic shield cylinder 6. Thus, in order to keep the magnetic shielding effect and prevent the problem, the magnetic shield cylinder 6 is separated from the distal end of the nozzle member 4 (the lower end of the distal-end member 13) by a predetermined distance L1 along the axial direction, of the nozzle member 4.

If electron beams start bending on the distal end of the nozzle member 4 in response to the influence of magnetism, the electron beams passing through the exit windows 3 are displaced less than electron beams that start bending in response to the influence of magnetism on the proximal portion of the nozzle member 4. The magnetic shielding effect of providing the magnetic shield member near the distal end of the nozzle member 4 is relatively small. The distance L1 may be set within a range where the magnetic shielding effect is relatively small.

Moreover, the distance L1 may be optionally adjusted depending on dimensions such as the diameter of the nozzle member 4, the operation conditions (electron beam intensity) of the electron beam irradiation apparatus, and so on.

For example, if the nozzle member 4 is 100 to 500 mm in length and 10 to 30 mm in diameter and the electron beam irradiation apparatus operates under the conditions of 80 to 200 kV and 1 to 80 mA, the ratio of the distance L1 to a length L2 in the axial direction of the nozzle member 4 (L1/L2×100) is preferably set at 15 to 35%.

If (L1/L2×100) is 35% or less, a sufficient region is obtained around the electron beam trajectory to the exit windows 3 of the magnetic shield cylinder 6, achieving a sufficient magnetic shielding effect. If (L1/L2×100) is 15% or more, the magnetic shield cylinder 6 is not affected by heat generated near the exit windows 3, achieving an excellent magnetic shielding effect.

If the length L2 of the nozzle member 4 is about 400 mm, the distance L1 is, for example, about 100 mm.

The length of the distal-end member 13 in the axial direction of the nozzle member 4 is quite smaller than L1 and L2.

In the apparatus of the present embodiment, as shown in FIG. 1, a partition wall 9 is disposed to surround the exit windows 3 of the nozzle member 4 from the proximal portion of the nozzle member 4. Thus, an external space near the nozzle member 4 (a container sterilization space under the partition wall 9) is separated from that near the vacuum housing 1. A sealing member 10 disposed between the proximal portion of the nozzle member 4 and the partition wall 9 seals a space between the proximal portion of the nozzle member 4 and the partition wall 9. Sterilizing gas snob as hydrogen peroxide gas and ozone is introduced into the external space near the nozzle member 4 to sterilize the space. The magnetic shield cylinder 6 is placed in the nozzle member 4 that has a sealed structure with the thin film 3b disposed on the distal end of the nozzle member 4. This configuration completely separates the magnetic shield cylinder 6 from a sterilizing gas atmosphere outside the nozzle member 4, thereby preventing corrosion caused by sterilizing gas.

In the apparatus of the present embodiment, if the nozzle member 4 has a constant outside diameter D, the placement of the magnetic shield cylinder 6 in the nozzle member 4 (in the inner nozzle cylinder 4a) can increase the internal cross-sectional area of the inner nozzle cylinder 4a on the distal end of the nozzle member 4 where the magnetic shield cylinder 6 is not provided, as compared with an apparatus that includes the magnetic shield cylinder placed outside the nozzle member 4 (outer nozzle cylinder 4b). Thus, the exit windows can have a large area. This configuration can advantageously obtain the same sterilizing effect while suppressing a temperature rise of the support portion 3a.

Second Embodiment

Figure 5:
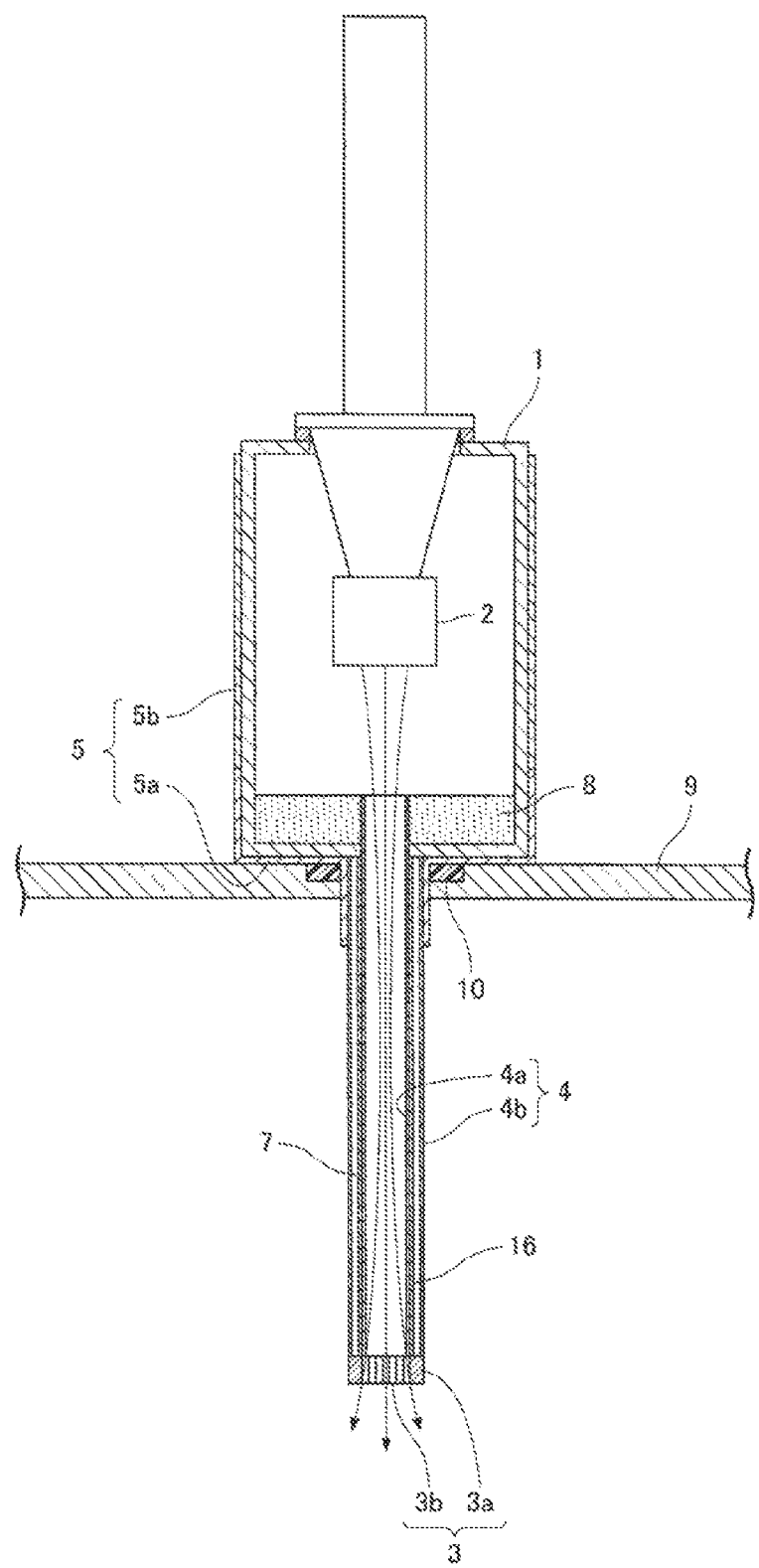
FIG. 5 is a front view showing a part of an electron beam irradiation apparatus in cross section according to a second embodiment of the present invention.
Figure 6:
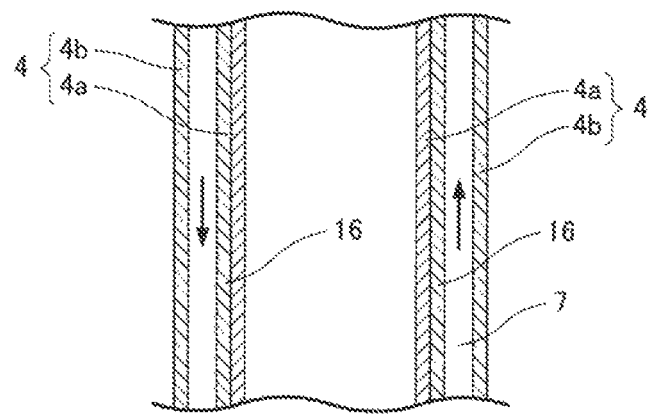
FIG. 6 is a cross-sectional view showing an enlarged part of a nozzle member in the electron beam irradiation apparatus of FIG. 5.

Referring to FIGS. 5 and 6, an electron beam irradiation apparatus according to a second embodiment of the present invent ion will be described, below. The same explanation as in the first embodiment is omitted.

As shown in FIG. 5, the electron beam irradiation apparatus includes a cylindrical vacuum housing 1 that is made of, for example, stainless steel and constitutes a vacuum chamber, an electron generator 2 provided in the vacuum housing 1, a cylindrical nozzle member 4 that is extended from the vacuum housing 1 so as to be inserted into a container from the neck of the container and has exit windows 3 on the distal end of the nozzle member 4, the exit windows being provided for emission of electron beams generated by the electron generator 2, and a magnetic shield member for the vacuum chamber (magnetic shield housing 5) and a magnetic shield member for the nozzle member which are respectively provided for the vacuum housing 1 and the nozzle member 4 so as to block variable magnetism generated around an electron beam trajectory extended from the electron generator 2 to the exit windows 3.

As shown in FIGS. 5 and 6, the magnetic shield member for the nozzle member includes a magnetic shield cylinder 16 having high magnetic permeability and covers the outer surface of an inner nozzle cylinder 4a. This configuration can suppress the influence of the magnetism of the earth or peripheral devices on an electron beam trajectory in the nozzle member 4.

Magnetic shield thin plates are placed to cover the outer side surfaces of the inner nozzle cylinder 4a and then are welded at predetermined points, so that the magnetic shield cylinder 16 is set in the nozzle member 4.

The magnetic shield cylinder 16 preferably has a thickness of 0.1 to 0.4 mm, more preferably 0.2 to 0.3 mm.

The magnetic shield cylinder 16 having a thickness of at least 0.1 mm can obtain a sufficient magnetic shielding effect on the electron beam trajectory in the nozzle member 4. If the magnetic shield cylinder 16 has a thickness of 0.4 mm or less, a sufficient space for a cooling flow path 7 can be obtained between the inner nozzle cylinder 4a and an outer nozzle cylinder 4b, thereby achieving an enhanced cooling effect on the nozzle member 4 and a support portion 3a.

The magnetic shield cylinder 16 is, for example, a Mumetal thin plate having a thickness of about 0.25 mm and relative permeability of about 90000.

As shown in FIGS. 5 and 6, the magnetic shield cylinder 16 is disposed between the inner nozzle cylinder 4a and the outer nozzle cylinder 4b, that is, in the cooling flow path 7. In this case, heat generated near the exit windows 3 during electron beam irradiation does not affect the magnetic shield cylinder 16. Thus, unlike in the first embodiment, the magnetic shield cylinder 16 does not need to be separated from a distal-end member 13 by a predetermined distance in consideration of the influence or heat. With this configuration, as shown in FIGS. 5 and 6, the magnetic shield cylinder 16 can be disposed to surround the entire region of the electron beam trajectory to the exit window 3 in the nozzle member 4.

Third Embodiment

Figure 7:
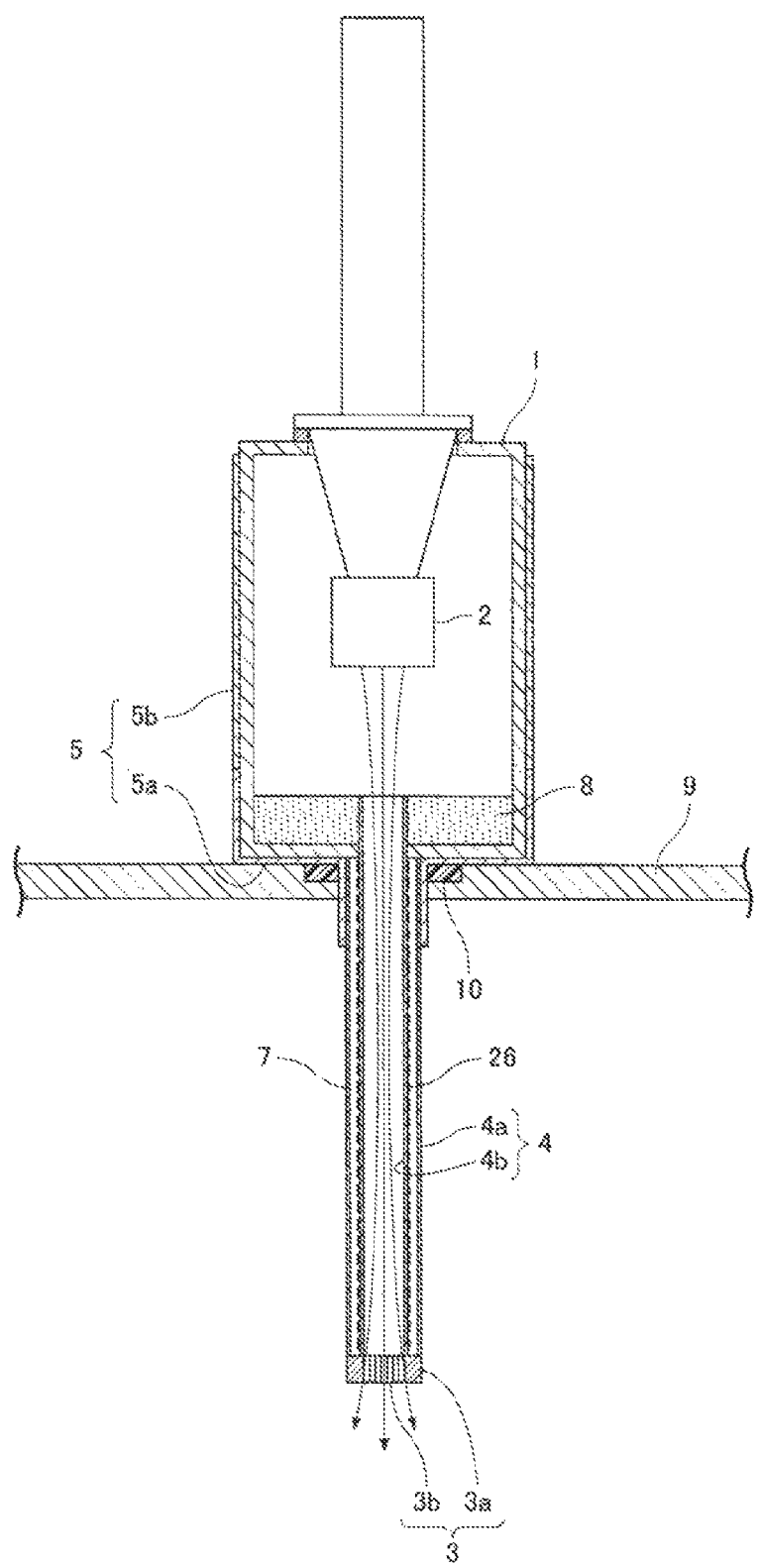
FIG. 7 is a front view showing a part of an electron beam irradiation apparatus in cross section according to a third embodiment of the present invention.
Figure 8:
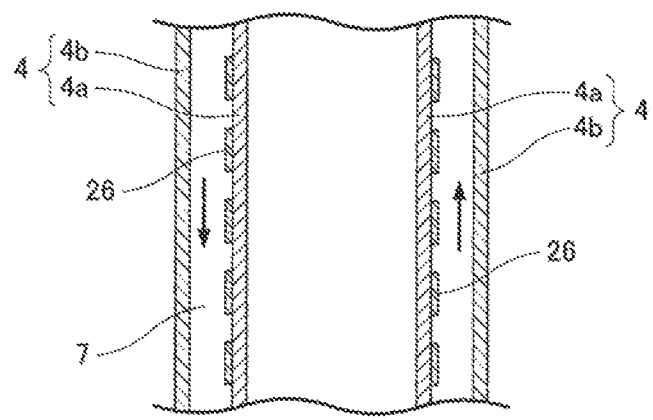
FIG. 8 is a cross-sectional view showing an enlarged part of a nozzle member in the electron beam irradiation apparatus of FIG. 7.
Figure 9:
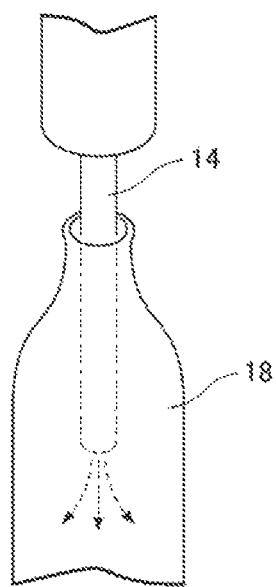
FIG. 9 shows that the nozzle of the electron beam irradiation apparatus is inserted into a container having a neck.

Referring to FIGS. 7 and 8, an electron beam irradiation apparatus according to a third embodiment of the present invention will be described below. The same explanation as in the first embodiment is omitted.

As shown in FIG. 7, the electron beam irradiation apparatus includes a cylindrical vacuum housing 1 that is made of, for example, stainless steel and constitutes a vacuum chamber, an electron generator 2 provided in the vacuum housing 1, a cylindrical nozzle member 4 that is extended from the vacuum housing 1 so as to be inserted into a container from the neck of the container and has exit windows 3 on the distal end of the nozzle member 4, the exit windows 3 being provided for emission of electron beams generated by the electron generator 2, and a magnetic shield member for the vacuum chamber (magnetic shield housing 5) and a magnetic shield member for the nozzle member 4 which are respectively provided for the vacuum housing 1 and the nozzle member 4 so as to block variable magnetism generated around an electron beam trajectory extended from the electron generator 2 to the exit windows 3.

As shown in FIGS. 7 and 8, the magnetic shield member for the nozzle member includes magnetic shield rings 26 having high magnetic permeability and covers the outer surface of an inner nozzle cylinder 4a. This configuration can suppress the influence of the magnetism of the earth or peripheral devices on an electron beam trajectory in the nozzle member 4.

The magnetic shield rings 26 are placed on the outer side surfaces of the inner nozzle cylinder 4a and then are welded at predetermined points so as to be set in the nozzle member 4.

In order to obtain a stable magnetic shielding effect, the magnetic shield rings 26 are preferably disposed at regular intervals.

The adjacent magnetic shield rings 26 are spaced at predetermined intervals so as to obtain a sufficient space for a cooling flow path 7 and a sufficient magnetic shielding effect on the electron beam trajectory in the nozzle member 4.

The magnetic shield ring 25 preferably has a thickness of 0.1 to 0.4 mm, more preferably 0.2 to 0.3 mm. The magnetic shield ring 26 having a thickness of at least 0.1 mm can obtain a sufficient magnetic shielding effect on the electron beam trajectory in the nozzle member 4. If the magnetic shield rings 26 have a thickness of 0.4 mm or less, a sufficient space for the cooling flow path 7 can be obtained between the magnetic shield rings 26 and an outer nozzle cylinder 4b, thereby achieving an enhanced cooling effect on the nozzle member 4 and a support portion 3a.

The magnetic shield rings 26 have a predetermined width so as to obtain a sufficient magnetic shielding effect on the electron beam trajectory in the nozzle member 4 and a sufficient space for the cooling flow path 7 between the adjacent magnetic shield rings 26.

In the third embodiment where the magnetic shield ring 26 is used, the space for the cooling flow path 7 between the inner nozzle cylinder 4a and the outer nozzle cylinder 4b can be wider than in the second embodiment where the magnetic shield cylinder 16 is used. This can achieve an improved cooling effect. Moreover, the magnetic shield ring 26 can be larger in thickness than the magnetic shield cylinder 16.

The magnetic shield ring 36 is, for example, a Mumetal annular member having a thickness of about 0.25 mm and relative permeability of about 90000.

As shown in FIGS. 7 and 8, the magnetic shield rings 26 are disposed between the inner nozzle cylinder 4a and the outer nozzle cylinder 4b, that is, in the cooling flow path 7. In this case, heat generated near the exit windows 3 during electron beam irradiation does not affect the magnetic shield rings 26. Thus, unlike in the first embodiment, the magnetic shield rings 26 do not need to be separated from a distal-end member 13 by a predetermined distance in consideration of the influence of heat. With this configuration, as shown in FIG. 5, the magnetic shield rings 26 can be disposed at regular intervals over the region of the electron beam trajectory to the exit windows 3 in the nozzle member 4.

The annular magnetic shield members used in the present embodiment may be disposed like a spiral or a smash, which can obtain the same effect as the annular magnetic shield members.

Fourth Embodiment

Figure 10:
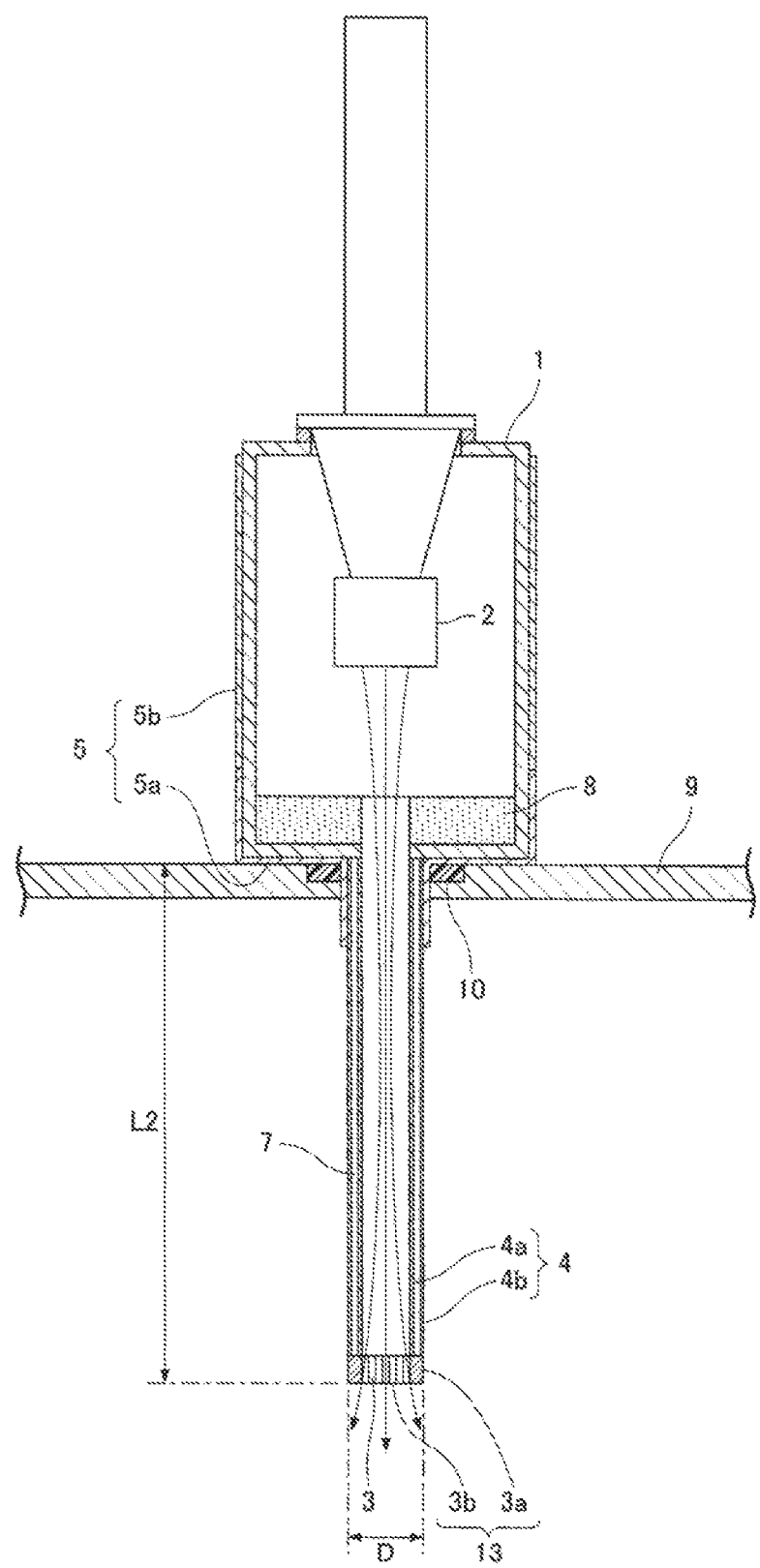
FIG. 10 is a front view showing a part of an electron beam irradiation apparatus in cross section according to a fourth embodiment of the present invention.

Referring to FIG. 10, an electron beam irradiation apparatus according to a fourth embodiment of the present invention will be described below. The same explanation as in the first embodiment is omitted.

As shown in FIG. 10, the electron beam irradiation apparatus does not include a magnetic shield member (magnetic shield cylinder 6) for a nozzle member, the magnetic shield member being provided in the electron beam irradiation apparatus according to the first embodiment.

Specifically, as shown in FIG. 10, the electron beam irradiation apparatus includes a cylindrical vacuum housing 1 that is made of, for example, stainless steel and constitutes a vacuum chamber, an electron generator 2 provided in the vacuum housing 1, a cylindrical nozzle member 4 that is extended from the vacuum housing 1 so as to be inserted into a container from the neck of the container and has exit windows 3 on the distal end of the nozzle member 4, the exit windows 3 being provided for emission of electron beams generated by the electron generator 2, and a magnetic shield member for the vacuum chamber (magnetic shield housing 5) which is provided for the vacuum housing 1 so as to block variable magnetism generated around an electron beam trajectory extended from the electron generator 2 to the exit windows 3.

In the present embodiment, if the nozzle member 4 has a constant outside diameter D, the apparatus not including the magnetic shield member (magnetic shield cylinder 6) for the nozzle member can slightly increase the diameter of an electron beam trajectory as compared with the apparatus including the magnetic shield member (magnetic shield cylinder 6) for the nozzle member. This configuration can advantageously reduce the influence of magnetism.

If the outside diameter D of the nozzle member 4 is kept constant, the cross-sectional area of a cooling flow path can be increased so as to raise an electron beam output.

The apparatus of the present embodiment does not include the magnetic shield member (magnetic shield cylinder 6) for the nozzle member, thereby further reducing the amount of released gas (gas generated in a vacuum in the entire apparatus. Thus, a vacuum level can be increased in the vacuum housing 1. This configuration can advantageously emit electron beams with stability, reduce discharge, and increase the lives of devices in the vacuum housing 1. Furthermore, the absence of the magnetic shield member (magnetic shield cylinder 6) for the nozzle member can simplify the manufacturing process of the electron beam irradiation apparatus.

The invention claimed is:

1. An electron beam irradiation apparatus that emits an electron beam into a container, the electron beam irradiation apparatus comprising:

a vacuum chamber;

an electron generator provided in the vacuum chamber;

a cylindrical nozzle member that is extended from the vacuum chamber so as to be inserted into the container and has exit windows on a distal end of the nozzle member, the exit windows being provided for emission of an electron beam generated by the electron generator into the container; and a magnetic shield member for the vacuum chamber, the shield member being provided for the vacuum chamber so as to block variable magnetism generated around an electron beam trajectory extended from the electron generator to the exit windows.

2. The electron beam irradiation apparatus according to claim 1, further comprising a magnetic shield member for the nozzle member, the shield member being provided for the nozzle member so as to block variable magnetism generated around the electron beam trajectory extended front the electron generator to the exit windows.

3. The electron beam irradiation apparatus according to claim 2, wherein the magnetic shield member for the vacuum chamber and the magnetic shield member for the nozzle member are made of a high permeability material having relative permeability of at least 50000.

4. The electron beam irradiation apparatus according to claim 3, wherein the magnetic shield member for the nozzle member is disposed to surround the electron beam trajectory.

5. The electron beam irradiation apparatus according to claim 4, wherein the magnetic shield member for the nozzle member is disposed in a shape like one of a cylinder, a ring, and a spiral relative to an axis of the nozzle member.

6. The electron beam irradiation apparatus according to claim 3, wherein the magnetic shield member for the nozzle member is disposed inside the nozzle member and is separated from a distal end of a nozzle by a predetermined distance along an axial direction of the nozzle so as to prevent heat generated near the exit windows during electron beam emission and transmitted to the magnetic shield member for the nozzle member from reducing the relative permeability of the magnetic shield member for the nozzle member.

7. The electron beam irradiation apparatus according to claim 3, wherein the magnetic shield member for the nozzle member and a cooling flow path for passage of a medium for cooling the nozzle member are provided on a side of the nozzle member.

8. The electron beam irradiation apparatus according to claim 2, wherein the magnetic shield member for the nozzle member is disposed to surround the electron beam trajectory.

9. The electron beam irradiation apparatus according to claim 8, wherein the magnetic shield member for the nozzle member is disposed in a shape like one of a cylinder, a ring, and a spiral relative to an axis of the nozzle member.

10. The electron beam irradiation apparatus according to claim 2, wherein the magnetic shield member for the nozzle member is disposed inside the nozzle member and is separated from a distal end of a nozzle by a predetermined distance along an axial direction of the nozzle so as to prevent heat generated near the exit windows during electron beam emission and transmitted to the magnetic shield member for the nozzle member from reducing the relative permeability of the magnetic shield member for the nozzle member.

11. The electron beam irradiation apparatus according to claim 2, wherein the magnetic shield member for the nozzle member and a cooling flow path for passage of a medium for cooling the nozzle member are provided on a side of the nozzle member.

* * * * *

UNITED STATES PATENT AND TRADEMARK OFFICE
CERTIFICATE OF CORRECTION

PATENT NO. : 9,601,224 B2
APPLICATION NO. : 14/785091
DATED : March 21, 2017
INVENTOR(S) : Ichiro Sakai et al.

It is certified that error appears in the above-identified patent and that said Letters Patent is hereby corrected as shown below:

On the Title Page

Item (72) Inventors should read:
Ichiro Sakai, Osaka (JP); Takayasu Yokobayashi, Osaka (JP);
Kaveh Bakhtari, Cambridge, MA (US)

Signed and Sealed this
Twenty-seventh Day of February, 2018

Andrei Iancu
*Director of the United States Patent and Trademark Office*